United States Patent
Meuli et al.

Patent Number: 5,370,695
Date of Patent: Dec. 6, 1994

[54] METAL SHANK

[75] Inventors: Hans C. Meuli, Bern; Hansjörg Koller, Winterthur, both of Switzerland

[73] Assignees: Sulzer Medizinaltechnik AG, Winterthur; Protek AG, Muensingen-Bern, both of Switzerland

[21] Appl. No.: 42,410

[22] Filed: Apr. 2, 1993

[30] Foreign Application Priority Data

Apr. 3, 1992 [EP] European Pat. Off. ........ 92810253.2

[51] Int. Cl.$^5$ ............................................. A61F 2/28
[52] U.S. Cl. .................................. 623/16; 623/23; 623/18; 433/173
[58] Field of Search ................ 623/16, 18, 21; 433/172, 173, 174, 175

[56] References Cited

U.S. PATENT DOCUMENTS

| Re. 31,865 | 4/1985 | Roux | 623/18 |
|---|---|---|---|
| 2,449,522 | 9/1948 | White | 433/173 |
| 2,721,387 | 10/1955 | Ashuckian | 433/173 |
| 3,576,074 | 4/1971 | Gault | 433/175 |
| 3,717,932 | 2/1973 | Brainin | 433/173 |
| 3,793,650 | 2/1974 | Ling et al. | 623/18 |
| 4,253,843 | 3/1981 | Staubli | 433/173 |
| 4,468,201 | 8/1984 | Fukuyo | 433/173 |
| 4,725,280 | 2/1988 | Laure | 623/21 |
| 4,759,768 | 7/1988 | Hermann et al. | 623/21 |
| 5,047,059 | 9/1991 | Saffar | 623/21 |
| 5,197,990 | 3/1993 | Lawes, et al. | 623/18 |
| 5,217,498 | 6/1993 | Henssge et al. | 623/18 |
| 5,290,311 | 3/1994 | Baumann | 623/18 |

FOREIGN PATENT DOCUMENTS

| 0115564 | 8/1984 | European Pat. Off. . |
| 0280424 | 2/1988 | European Pat. Off. . |
| 2309432 | 11/1973 | Germany . |
| 0728855 | 5/1980 | U.S.S.R. ...... 433/173 |

*Primary Examiner*—David Isabella
*Attorney, Agent, or Firm*—Townsend and Townsend Khourie and Crew

[57] ABSTRACT

Shanks designed especially for small joints, for example, finger joints, and having a rectangular cross-section of core (1), exhibit towards their free end plastically deformable lobes (7) of pieces of sheetmetal which may be deformed, e.g., bent intraoperatively, for which they are subdivided at intervals in the axial direction into a number of sections (7a) through cuts (8) running perpendicular to the axis (9) of the shank.

4 Claims, 1 Drawing Sheet

METAL SHANK

BACKGROUND OF THE INVENTION

For implants in medullated bones of small Joints in particular, it is frequently necessary for the anchoring, especially for the primary anchoring, to keep ready a plurality of different sizes and shapes of shank in order to be able to respond in an optimum way to the individual characteristics of the individual patients and thereby above all during the first time after the implant, to guarantee a firm seat of the shank. This has previously demanded for every small Joint a large "assortment" of shanks differing little from one another; since in the case of small Joints the actual Joint part is usually connected inseparably to the shank, in the case of the known constructions of implant, even for every case a plurality of Joint prostheses have therefore to be made ready.

SUMMARY OF THE INVENTION

The problem underlying the invention is to reduce the considerable outlay described and to create especially for small joints a shank which within a certain range is adaptable intraoperatively to different shapes and sizes of bone of different patients. The solution of this problem is effected by the shank exhibiting towards its free end plastically deformable sheetmetal lobes which project from the corners of the core and are subdivided into a number of sections through a number of cuts running at least approximately perpendicularly to the axis of the shank.

The plastically deformable lobes subdivided in the axial direction enable the operating surgeon to alter the position of its individual sections relative to the core of the shank during the operation, for example, to bend them by narrow flat pliers adapted to the height of their sections and thus anchor them, for example, by jamming in a given bone cavity. The alteration of the shape of the anchoring is carried out intraoperatively without the generation of chips of metal.

A simplification in the production of the new shank follows if for every two corners of the cross-section the lobes are combined into a tub-shaped piece of sheetmetal which in turn is fastened to one sideface of the cross-section of core. Moreover for the intraoperative adaptation of the sections of lobe it is useful if the height of the sections of lobe is constant in the axial direction. An insertion of the shank into a tapering bone cavity is facilitated if the distance of the edges of the lobes from the core increases steadily from distal to proximal. The lobes bent out in different directions from one another are stressed elastically during driving in and dig into the bone tissue.

Preferred materials for the new shank and lobes are titanium and titanium alloys. The cuts in the lobes perpendicular to the axis of the shank may, for example, be produced by water jet cutting, by wire cutting by means of spark erosion or by stamping. Moreover the fastening of the pieces of sheetmetal to the core is effected very simply by welding, while the tub shape may be generated before or after the welding.

BRIEF DESCRIPTION OF THE DRAWINGS

The invention is explained in greater detail below with the aid of an embodiment in connection with the drawing.

DESCRIPTION OF THE SPECIFIC EMBODIMENTS

Figure 2:
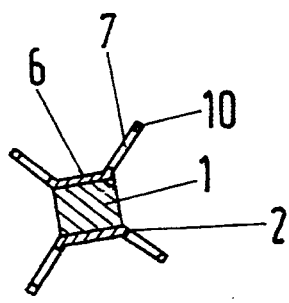
FIG. 2 is a section II—II cross-sectional view of the shank from FIG. 1.
Figure 1:
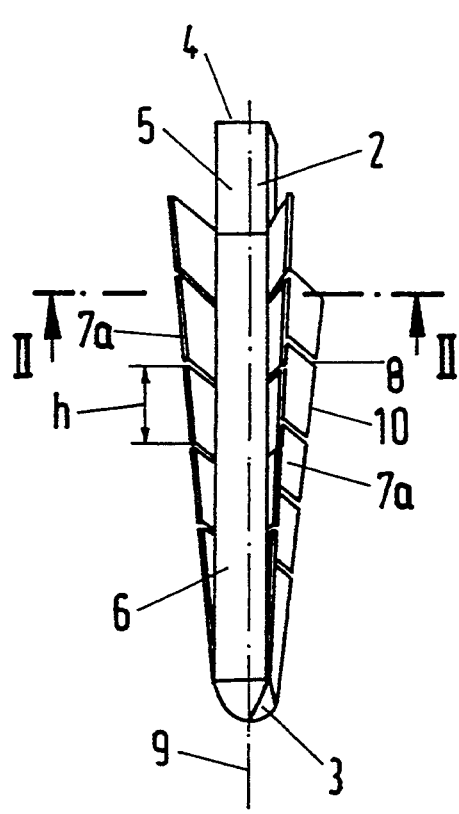
FIG. 1 shows in perspective an elevation of the new shank.

The core 1 of the shank is rectangular (FIG. 2) or square in cross-section and over its whole height has a constant length of side. Distally its four edges 2 run together into a rounded endpiece 3. At the proximal end 4 of the four-edged core 1 is seated the actual Joint part of the prosthesis, which is not represented in the example shown.

To each of two sides 5 of the core 1 lying opposite one another is fastened, e.g., welded, a piece 6 of sheetmetal bent up into the shape of a tub.

Figure 3:
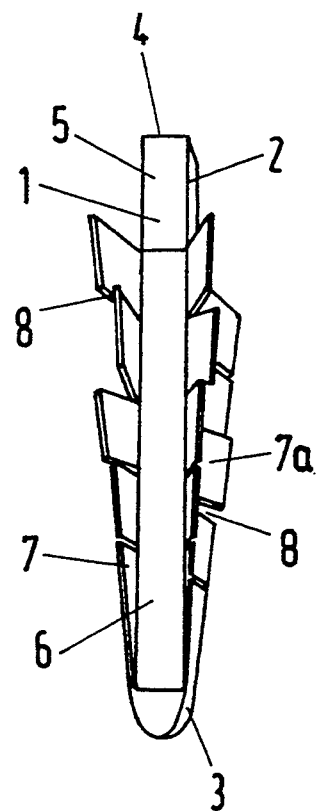
FIG. 3 illustrates the intraoperatively "altered" shank of FIG. 1.

The two bent-up endpieces of the piece 6 of sheetmetal form plastically deformable lobes 7 which at delivery of the shanks are aligned at least essentially in the direction of the diagonals of the rectangular cross-section of core. Through a number of cuts 8 arranged at a distance apart over the height of the shank the lobes 7 are subdivided in the direction of the axis 9 of the shank into a number of sections 7a which during the operation can be deformed individually, for example, by bending with flat pliers—as illustrated in FIG. 3. The cuts 8 run at least approximately in planes perpendicular to the axis 9 of the shank, with the cuts 8 for all four lobes 7 lying in the example shown at the same height and their intervals h in the axial direction being likewise the same.

In order to facilitate the insertion of the shank into the operatively prepared cavity in the bone, the distances of the edges 10 of the lobes from the edges 4 of the cross-section of core increase steadily in the direction from distal to proximal.

We claim:

1. A metal shank for an implant in a hollow bone comprising:
   a core having a rectangular cross-section with corners, an axis and a distal end; and
   plastically deformable sheetmetal lobes projecting from the corners of the core near the distal end, each lobe having at least one slit subdividing the lobe into a plurality of sections and oriented generally perpendicular to the axis of the shank.

2. The shank of claim 1 wherein the lobes comprise channel-shaped pieces of sheetmetal fastened to a sideface of the core.

3. The shank of claim 1 wherein the lobes have equal axial lengths.

4. The shank of claim 1 wherein the lobes each extend a distance from the core, the distances increasing from the distal end to a proximal end of the core.

* * * * *